United States Patent [19]

Akiyama

[11] Patent Number: 5,013,146
[45] Date of Patent: May 7, 1991

[54] OPTHALMOLOGICAL MEASUREMENT APPARATUS

[75] Inventor: Koichi Akiyama, Tsukuba, Japan
[73] Assignee: Kowa Company Limited, Japan
[21] Appl. No.: 396,639
[22] Filed: Aug. 18, 1989
[30] Foreign Application Priority Data Sep. 14, 1988 [JP] Japan .................. 63-228485

[51] Int. Cl.⁵ .................. A61B 3/14; A61B 3/10
[52] U.S. Cl. .................. 351/208; 351/214; 351/221
[58] Field of Search .............. 351/205, 208, 221, 214; 606/4, 5, 6

[56] References Cited

U.S. PATENT DOCUMENTS 4,702,576 10/1987 Magnante .................. 351/221
4,834,527 5/1989 Kobayashi .................. 351/208

Primary Examiner—Rodney B. Bovernick
Attorney, Agent, or Firm—Bruce L. Adams; Van C. Wilks

[57] ABSTRACT

Disclosed is an ophthalmological measurement apparatus in which a laser beam is directed into an eye under examination and a measurement value is output on the basis of the state of scattering of the laser beam within the eye. An alignment index projector is provided for forming an alignment index for use in judging alignment between the apparatus and the eye under examination, whose relative position is controlled to cause light scattering points produced at the eye by the laser beam and the light of the alignment index image to assume predetermined positions within the field of an observation. The apparatus can be used for measuring protein concentration in the anterior chamber of the eye or as a split lamp microscope and enables easy alignment between itself and the eye being examined.

13 Claims, 5 Drawing Sheets

OPTHALMOLOGICAL MEASUREMENT APPARATUS

BACKGROUND OF THE INVENTION

1. Field of the Invention

This invention relates to an ophthalmological measurement apparatus and more particularly to an ophthalmological measurement apparatus which projects a laser beam into the eye to be examined and outputs a specific measured value based on the state of scattering of the laser beam within the eye.

2. Description of the Prior Art

Measurement of protein concentration within the anterior chamber of the eye is highly important in determining the presence of inflammation within the eye, namely whether or not a blood-aqueous barrier functions normally. Conventionally, the general practice has been to use a slit lamp microscope and to make the determination by visual observation on the basis of grading. While a quantitative method based on photographic measurement has been reported, the fact remains that no easy method for clinical application has yet been developed.

Where judgment is based on visual observation, the judgment standards will differ from one person to another, degrading the credibility of the data obtained. For overcoming this problem, there is used a method of ophthalmological measurement in which a laser beam is directed into the eye and the light scattered within the eye is quantitatively analyzed (see U.S. Pat. Nos. 4,711,542 and 4,832,043, for example).

Where a laser beam is used for ophthalmological measurement, however, the intensity of the scattered light is extremely weak. The results of the measurement are therefore easily affected by noise components, i.e. by any light present other than the light to be measured. For example, if the measurement is carried out with respect to the anterior chamber and the point of measurement is too close to the crystalline lens, light scattered by the lens will constitute noise and the results of the measurement will vary depending on the location.

Moreover, the cornea has a strong lens effect and any light other than that impinging normally thereon is refracted thereby. This means that the amount of refraction varies with the point of impingement, with the result that the relationship between the point of measurement (the convergence point of the laser beam) and the point where the light is received (the mask) deviates. As the depth of the humor aqueous in the anterior chamber is about 3 mm, it is necessary to focus the laser beam at an intermediate portion lying at a depth of between 1 and 2 mm and to receive the light scattered from this measurement point with high accuracy. This requires accurate alignment between the apparatus and the eye under examination, particularly in the horizontal direction, and also makes it necessary to have a method for confirming that the required state of alignment has been achieved.

The present invention was accomplished in view of these circumstances and its object is to provide an ophthalmological measurement apparatus which enables alignment between the eye under examination and the apparatus to be obtained with ease.

SUMMARY OF THE INVENTION

The present invention provides an ophthalmological measurement apparatus in which a laser beam is directed into an eye under examination and a measurement value is output on the basis of the state of scattering of the laser beam within the eye under examination. The apparatus comprises a laser beam projection section for focusing a laser beam produced by a laser beam source at a predetermined point within an eye under examination, a light receiving section equipped with a photoelectric conversion element for receiving scattered laser light from the eye under examination, an alignment index projection section for forming at a predetermined point within the eye under examination an alignment index for use in judging alignment between the apparatus and the eye under examination, an observation section for observing the state of the laser beam and of light of the alignment index image at the eye under examination, and means for controlling the relative position between the eye under examination and the apparatus to cause light scattering points produced at the cornea of the eye under examination by the laser beam and the light of the alignment index image to assume predetermined positions within the field of the observation section.

Moreover, the observation section of the apparatus can be constituted to have indices which indicate the positions which the light scattering points at the eye cornea of the laser beam and the light of the alignment index image should assume within the field of the observation section when the relative positions of the apparatus and the eye under examination are in the predetermined alignment. The colors of the laser beam and the light of the alignment index image are preferably made different. Preferably, the alignment index projection section and the light receiving section have at least part of their optical paths in common.

Moreover, a slit beam projection section is provided which can be positioned with respect to the eye under examination independently of the laser beam projection section, the light receiving section and the alignment index projection section, whereby the apparatus is also made usable as a slit lamp microscope.

With such an arrangement, the light scattering points produced on the cornea of the eye under examination by the laser beam and the light of the alignment index image intrinsically assume the predetermined positions when the apparatus and the eye under examination are in the predetermined alignment. Thus the state of alignment between the apparatus and the eye under examination can be evaluated from the position of the light scattering points with ease.

Further, the judgment regarding alignment is additionally facilitated by providing indices indicating the positions within the field of the observation section that the light scattering points produced by the laser beam and the light of the alignment index image intrinsically assume when alignment is achieved. It is further advantageous, particularly when an arrangement is used in which the laser beam and the light of the alignment index image are of different colors. Moreover, a more compact apparatus can be realized with greater freedom of design by having the alignment index projection section and the light receiving section share at least part of the same optical path.

Still further, by providing a slit beam projection section which can be positioned with respect to the eye under examination independently of the laser beam projection section, the light receiving section and the alignment index projection section, the apparatus is also made usable as a slit lamp microscope.

BRIEF DESCRIPTION OF THE DRAWINGS

The objects and features of the present invention will become more apparent from a consideration of the following description taken in conjunction with the accompanying drawings in which.

DETAILED DESCRIPTION OF THE PREFERRED EMBODIMENTS

The invention will now be described with reference to the attached drawings.

Figure 1:
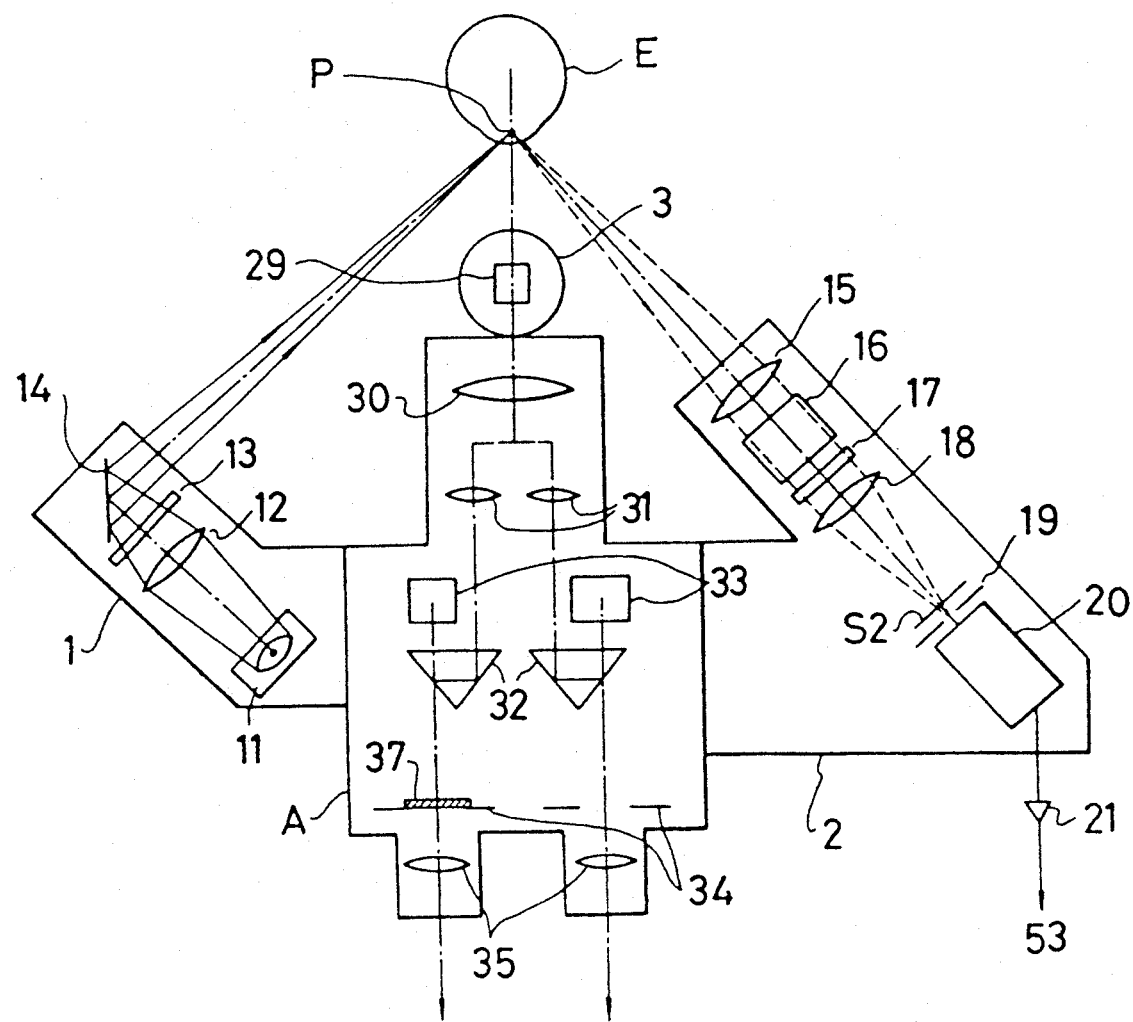
FIG. 1 is a schematic view of an ophthalmological measurement apparatus according to this invention as seen from above.

FIG. 1 is a top view of an ophthalmological measurement apparatus in accordance with the present invention. The apparatus is constituted mainly of four sections designated by reference numerals 1 to 4. Reference numeral 1 denotes a laser beam projection section comprising a semiconductor laser or other such light source (not shown), a mirror 11, a lens 12, a polarizing plate 13, and a mirror 14. A laser beam advancing perpendicularly to the surface of the drawing sheet impinges on the mirror 11, advances through the polarizing plate 13, and is reflected by the mirror 14 to converge at convergence point P in the anterior chamber of the eye under examination E. The alignment between the eye under examination and the measurement apparatus will be described later.

Reference numeral 2 denotes a light receiving section which receives light scattered from the vicinity of the convergence point P and comprises a lens 15, a beam splitter 16 for coupling with an alignment index projection optical system to be explained later, an interference filter 17, a lens 18, a shutter S2, a mask 19 and a photomultiplier 20. The interference filter 17 is constituted as a narrow-band interference filter whose peak wavelength is the same as the wavelength of the laser beam produced by the laser beam projection section 1. The mask 19 is for cutting extraneous light from unrequired regions, and the mask 19 and the convergence point P are positioned conjugately with respect to the optical system of the light receiving section 2.

Reference numeral 3 denotes a slit beam projection section located forward of an observation section 4 and serves to form a slit image at the convergence point P within the eye under examination E. In FIG. 1, the main elements of the slit beam projection section 3 are disposed perpendicularly to the drawing sheet so that in this figure the only element shown is a prism 29 for reflecting the slit beam in the direction of the eye under examination E. As will be explained in more detail later, the slit beam projection section 3 is constituted so as to be movable independently of the laser beam projection section 1, the light receiving section 2 and the observation section 4, whereby the apparatus can also be used as a slit lamp microscope.

The observation section 4 has two eyepieces 35, 35, making it possible for the operator 36 to view the measurement region with both eyes and also, as will be explained more completely later, for him to confirm the state of alignment during the alignment operation. In addition to the eyepieces 35, 35, the observation section 4 comprises lenses 30, 31, prisms 32, 33 and field stops 34. At the position of the field stop field 34 on the left side as seen in FIG. 1, there is provided an alignment confirmation index plate 37. (The alignment confirmation index plate 37 bears two indices and will be described in detail below.)

As shown in FIG. 1, the laser beam projection section 1 and the light receiving section 2 are fixed to the observation section 4 such that their optical axes intersect at the eye under examination E at an angle of approximately 90 degrees.

The laser beam projection section 1, the light receiving section 2 and the slit beam projection section 3 will now be explained in detail with reference to FIGS. 2 to 4.

Figure 2:
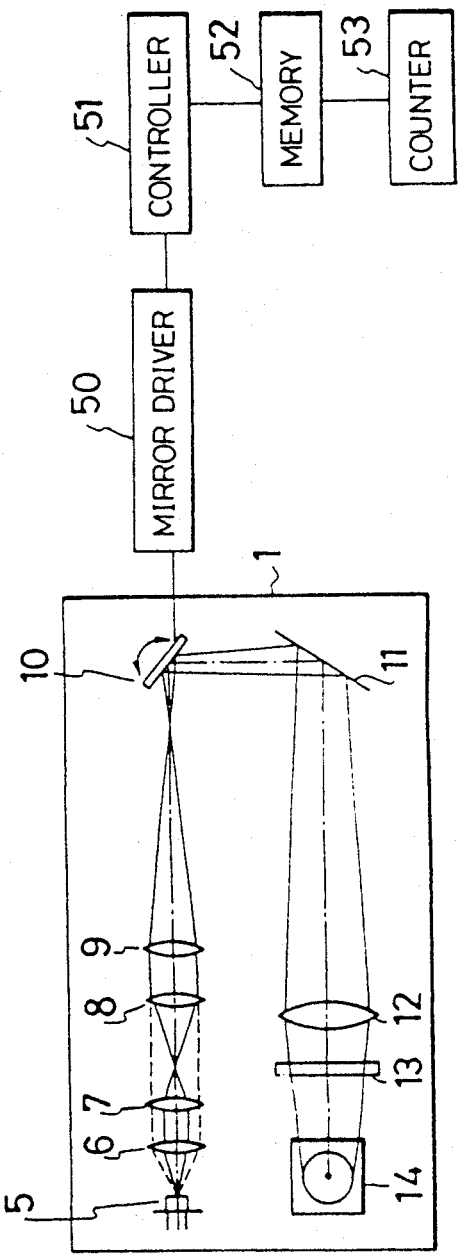
FIG. 2 is a schematic view of the laser beam projection section of the apparatus of FIG. 1 as seen from the side.

The structure of the laser beam projection section 1 is shown in FIG. 2. The laser beam from a semiconductor laser 5 serving as a light source is converted into a parallel beam by a collimator 6 and then is formed into a circular parallel beam by an elliptical beam expander constituted of lenses 7 and 8. It then proceeds through a relay lens 9 and a movable mirror 10 to the mirror 11. The movable mirror 10 is driven by a motor or the like for angular adjustment.

The angular position of the movable mirror 10 is controlled by a controller 51 through a mirror drive circuit 50, whereby the laser beam is deflected to scan the measurement area around the convergence point P.

The controller 51 is constituted of a microprocessor or the like and is connected with a memory 52 for use in computing the mirror angle and other control operations. The memory 52 is connected with a counter 53 for processing of the output of the light receiving section 2.

Further, the polarizing plate 13 serves to maintain the direction of polarization of the laser beam constant and is also used for enabling the quantity of light to be regulated by rotation of the semiconductor laser at the time of initial setup.

This will be explained. The semiconductor laser can be directly modulated and thus the quantity of light emitted thereby can be controlled by regulating the amount of electric current injected. However, this is not practical because at the time of directing the laser beam into the eye under examination, it is necessary to drop its power to around 30 microwatts, for example, and if the power is lowered to this level by controlling the injection current, the operation itself becomes unstable, thus increasing non-laser oscillation with a single mode oscillation being changed into a multi-mode oscillation. Instead, therefore, the initial setting is carried out by rotating the laser (because the semiconductor laser produces a linearly polarized beam), and fluctuations in the power are thereafter corrected by direct modulation.

Figure 3:
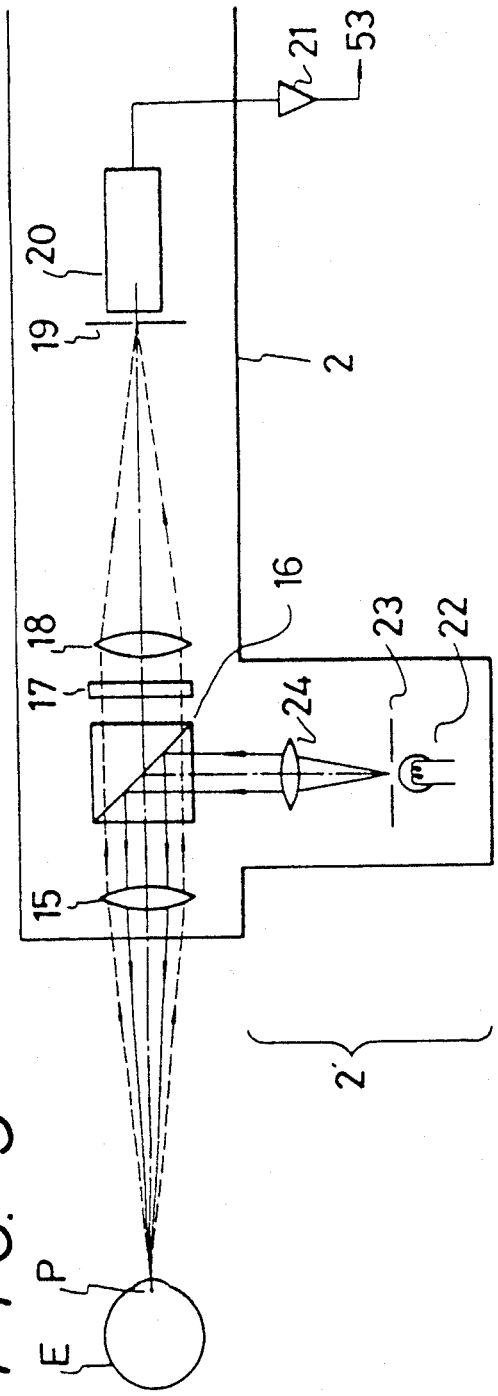
FIG. 3 is a schematic view of the light receiving section and an alignment index projection section of the apparatus of FIG. 1.

FIG. 3 is a side view showing the structures of the light receiving section 2 and the alignment index projection optical system located beneath this section.

In FIG. 3, the part indicated by the reference numeral 2', which is not illustrated in FIG. 1, is an optical system for producing and projecting an index for use in alignment. The optical system 2' comprises an alignment light source 22, alignment index plate 23 and a lens 24. The beam emitted by the alignment light source 22 should preferably be of a different color than the color of the laser beam produced by the laser beam projection section 1. The reason for this will be explained later.

The optical system 2' is coupled with the optical system of the light receiving section 2 by the beam splitter 16, and an image of the index of the alignment index plate 23 is formed at the convergence point P in the eye under examination E. As shown in the FIG. 3, the output of the photomultiplier 20 of the light receiving section 2 is input to the counter 53 shown in FIG. 2 via an amplifier 21.

Figure 4:
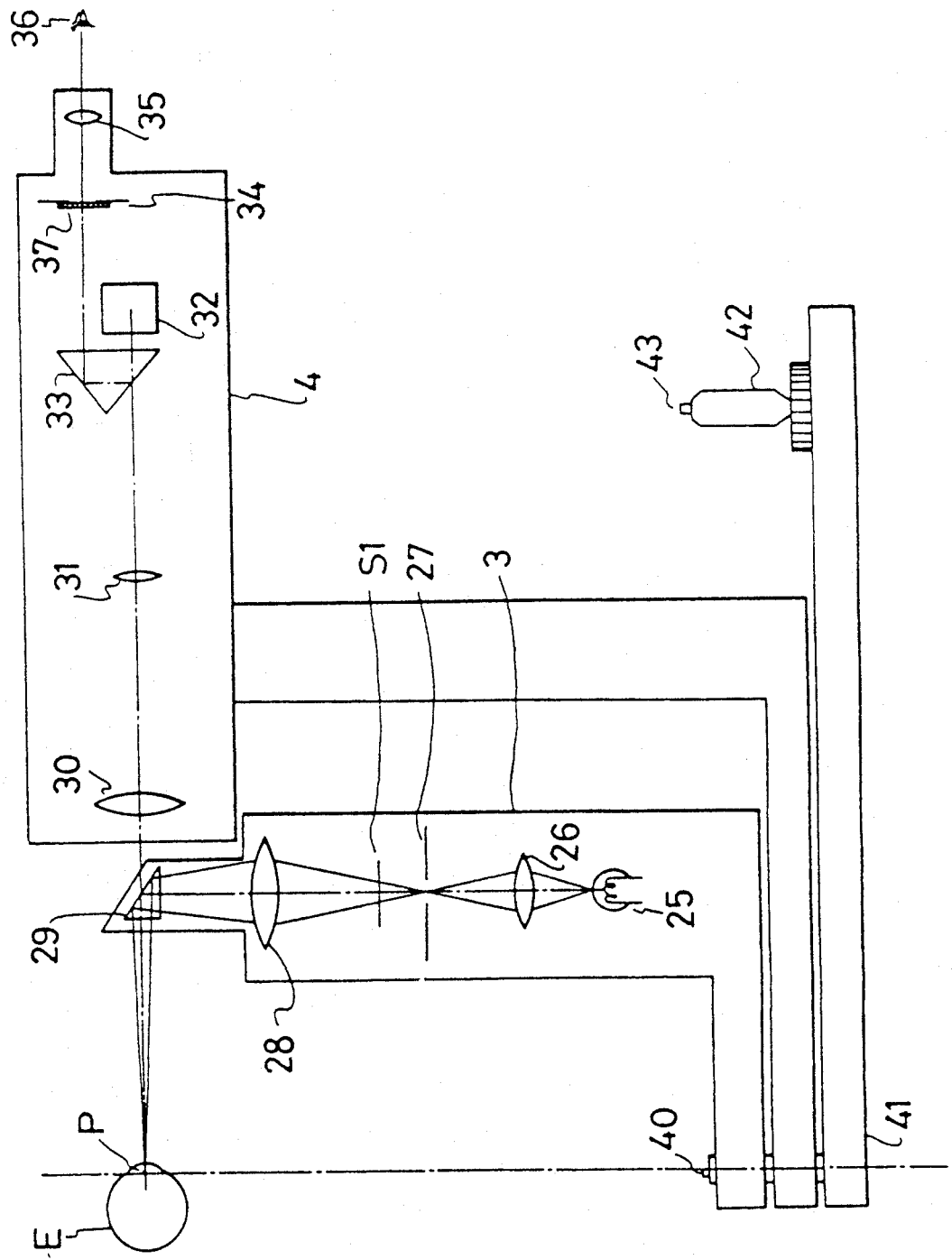
FIG. 4 is schematic view of an ophthalmological measurement apparatus according to the present invention as seen from the side.

FIG. 4 is an overall side view of the structure of the apparatus, including the slit beam projection section 3 and the observation section 4.

As illustrated, the slit beam projection section 3 and the observation section 4 (to which the laser beam projection section 1 and the light receiving section 2 are attached) are supported on respective L-shaped frames, which are in turn supported so as each to be rotatable in a horizontal plane about a shaft 40 rising from a platform 41.

By use of a joy stick 42, the platform 41 can be moved as a whole over the surface of a base (not shown) for the purpose of aligning the apparatus such that the axis of the shaft 40 passes through the convergence point P within the eye under examination E. The tip of the joy stick 42 has a switch 43 for controlling the insertion/extraction or opening/closing of the shutter S2 and a shutter S1 of the slit beam projection section 3. The structure of this type of operation system is known to the art and will not be explained in detail here.

The slit beam projection section 3 comprises a light source 25, a lens 26, a slit plate 27, the shutter S1, a lens 28 and the prism 29. The slit beam projection section 3 forms an image of the slit of the slit plate 27 at the convergence point P in the eye under examination E. This slit image illuminates the region surrounding the convergence point P of the laser beam from laser beam projection section 1, facilitating confirmation of the position of the convergence point P. Further, since the slit beam projection section 3 can rotate about the shaft 40 independently of the other sections, and specifically independently of the observation section 4, the apparatus can be used as a slit lamp microscope. In this case, the eye under examination can be observed in section through the observation section 4 using the slit beam.

FIG. 4 shows the structure relating to the observation section 4 in the vicinity of the optical axis on the left side of the observation section, where the alignment confirmation index plate 37 is provided. The reference numeral 36 in FIG. 4 indicates the eye of the person operating the apparatus.

An explanation will now be given of the procedures for achieving alignment between the apparatus and the eye under examination and of the overall flow of procedures during measurement. The operator rests the patient's chin on a chin rest of well-known structure (not shown) fixed on the base (not shown) of the apparatus and brings the apparatus and eye into preliminary alignment. He then turns on the light source 25 of the slit beam projection section 3, thus causing an image of the slit of the slit plate 27 to be projected onto the eye under examination E. He also focuses the laser beam from the laser beam projection section 1 at the convergence point P of the eye E. Next he turns on the alignment light source 22 to illuminate the alignment index plate 23 (which is of pinhole or like configuration), whereby the index is projected in the direction of the eye under examination E via the optical system of the light receiving section 2 (namely, via the beam splitter 16 and the lens 15).

Figure 5:
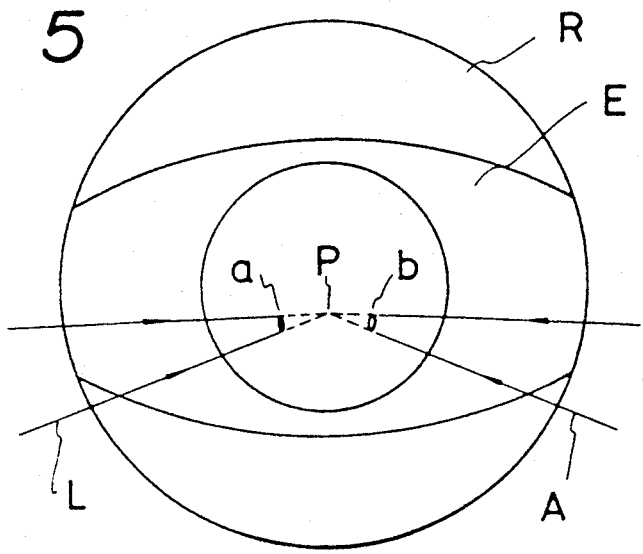
FIG. 5 is a schematic view showing the field of the observation section in the apparatus of FIG. 1.

Then while observing the slit image, the alignment index and the state of impingement of the laser beam through the observation section 4, he operates the joy stick 42 so as to move the platform 41 for bringing the eye E and the apparatus into proper positional alignment. FIG. 5 shows the image observed through the observation section 4 when the eye under examination E and the apparatus are properly positioned within a horizontal plane.

In FIG. 5, the reference symbol L designates the laser beam produced by the laser beam projection section 1 and the reference symbol A designates the light beam from the optical system 2' built in the light receiving section 2. As is clear from FIG. 1, the laser beam L and the alignment beam A intersect at an angle of about 90 degrees within the horizontal plane, meaning that the cornea of the eye under examination E receives the beams at angles of 45 degrees from left and right. At this time, light is scattered by the cornea, as indicated by the reference symbols a and b. If the positions of the light scattering points and coincide with predetermined positions within the field R of the observation section 4, it is judged that the alignment of the eye under examination E and the apparatus has been achieved.

Figure 9:
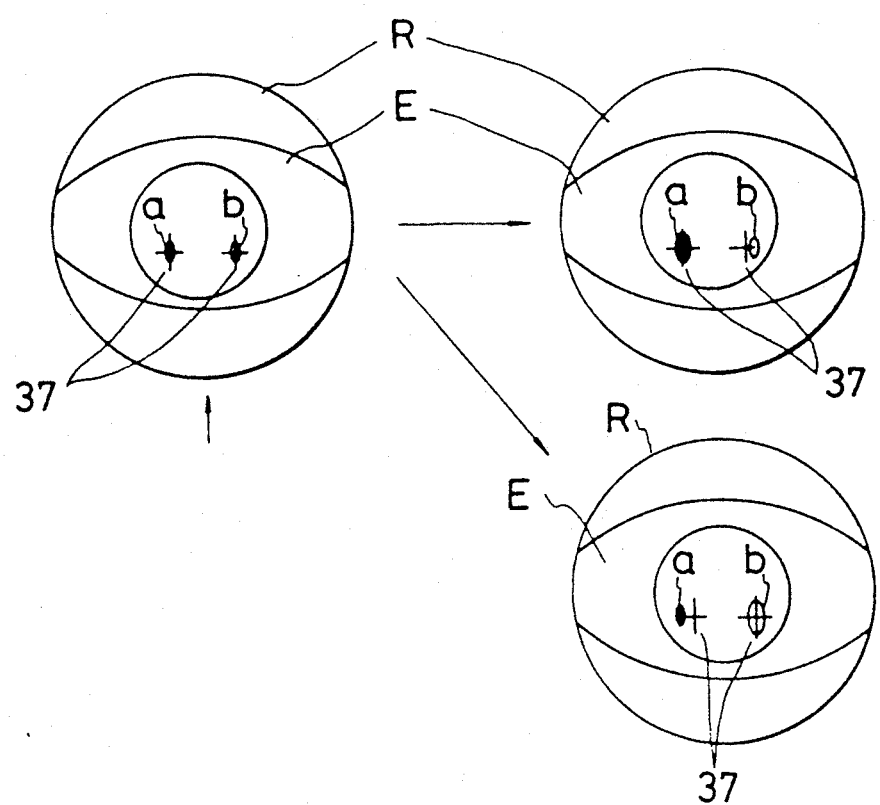
FIG. 9 is a diagram showing the field of the observation section in the case of misalignment in the apparatus of FIG. 1.

On the other hand, if the alignment is not correct, the image observed through the observation section 4 is such as shown on the right side in FIG. 9. The state shown on the left side of FIG. 9 is the same as that shown in FIG. 6 and is thus the image at the time of proper alignment. In contrast, the state shown at the upper right is that observed when the distance between the eye E and the apparatus along the x axis shown in FIG. 7 is too short and the position of the light scattering point b becomes offset to the outside, while the state shown at the lower right is that observed when the distance between the eye E and the apparatus along the y-axis in the same figure is too short and only the light scattering point a becomes offset to the outside.

Further as will be noted from the states shown on the right side of FIG. 9, a change occurs not only in the positions of the light scattering points a and b but also in their sizes. Where there is positional deviation in both the x and y directions in FIG. 7, it will become difficult to discern a change in the size of the light scattering region but the positional deviation will be easy to perceive. Thus if the light scattering points a and b coincide with the positions of the two alignment confirmation indices 37, it can be judged that alignment has been accomplished. Since there is only one position in the horizontal plane at which the light scattering points a and b are not reversed left and right and are positioned one at each of the alignment confirmation indices 37, positional alignment between the eye under examination E and the apparatus can be accomplished by a simple operation and with high accuracy.

Figure 6:
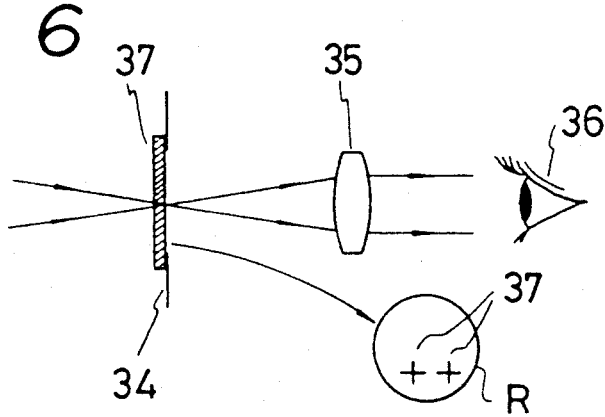
FIG. 6 is a schematic view showing the structure in the vicinity of an eyepiece of the observation section of the apparatus of FIG. 1.

For indicating the proper position of the light scattering points a and b, the alignment confirmation index plate 37 that is provided at the position of one of the field stops 34 is set in position in advance, as shown in FIG. 6. The alignment confirmation index plate 37 is constituted of, for example, optical glass and has two pairs of cross-hairs, as also shown in FIG. 6.

Figure 7:
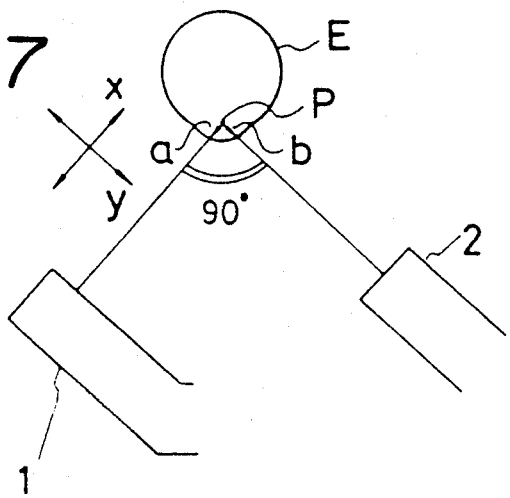
FIGS. 7 and 8 are views for explaining judgment regarding alignment in the apparatus of FIG. 1.
Figure 8:
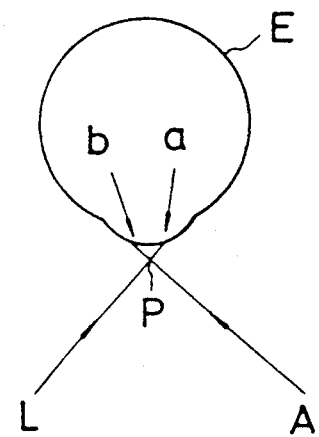

If the eye under examination E and the apparatus are properly positioned in the horizontal plane as shown in FIG. 7 and if the indices of the alignment confirmation index plate 37 of FIG. 6 are then made coincident with the light scattering points a and b (FIG. 5), then in the case where the eye under examination E and the apparatus are too far apart, the positions of the light scattering points a and b will reverse as shown in FIG. 8. Thus, if the laser beam L is red and the color of the alignment beam A is made a color other than red, such as green, it will be possible to judge the distance on the basis of the color of the scattered lights produced.

Since the alignment beam A is cut by the interference filter 17 provided in the light receiving section 2 and does not reach the photomultiplier 20, leaving the alignment light source 22 on constantly does not case any problems. On the other hand, if no interference filter 17 is provided, it suffices to turn off the alignment light source 22 when measurement is being conducted. Moreover, if as was mentioned earlier a light source (e.g. an LED) emitting green light is used as the alignment light source 22 and a laser emitting red light is used, it becomes easy to distinguish the scattered lights resulting from the respective beams. Further, since it is highly likely that accurate measurement results will not be obtained if the red light passes through the green point b during the measurement, this arrangement is also useful as regards judging whether or not the measurement was carried out accurately.

As the alignment index is conjugate with the convergence point P and the mask 19 is also conjugate with convergence point P, the convergence point of (for example) the green light (the alignment beam A) represents the image point of the mask 19. With the aforesaid arrangement, the convergence point of the laser beam and the convergence point of the alignment beam A should coincide at the convergence point P (where the beams intersect at 90 degrees) and if they do not, this indicates an apparatus setting error (or a malfunction).

After alignment has been accomplished in the foregoing manner, if the switch 43 of the joy stick 42 shown in FIG. 4 is depressed, the shutter S1 will close and the shutter S2 will open so that the light of the laser beam produced by the laser beam projection section 1 which is scattered by protein in the anterior chamber will enter into and be measured by the light receiving section 2, making it possible to measure the protein concentration in the anterior chamber of the eye under examination.

In this measurement, a laser beam is directed from the laser beam projection section 1 to the convergence point P within the eye under examination E, while the scattered light in the vicinity of the convergence point P is received by the light receiving section 2. The output of the photomultiplier 20 is passed through the amplifier 21 to the counter 53 connected with the controller 51. In the counter 53, the intensity of the scattered light is represented and counted as the number of pulses per unit time. The count data of the counter 53, namely the number of the sampling and the total count, are stored at a predetermined memory region in the memory 52 once every time unit. The controller 51 carries out computations on the basis of this measurement data stored in the memory 52, whereby the protein concentration in the anterior chamber is determined. As the processing for this determination is well known, it will not be explained here.

The above-described embodiment is arranged such that the alignment between the eye under examination E and the apparatus can be detected from whether or not the points at which the lights from the laser and alignment beams are scattered coincide with predetermined positions within the observation field of the observation optical system. As a result, the alignment between the eye under examination and the apparatus can be carried out simply and reliably.

Moreover, since a semiconductor laser is used as a light source and also since the light receiving section 2 and the alignment optical system 2' use a common optical system, the various sections of the apparatus according to the foregoing embodiment can be made compact, and the laser beam projection section 1 and the light receiving section 2 can be readily attached to the observation section 4 to combine these sections into an integrated unit.

The following are some of the advantages of using a semiconductor laser as the laser beam source:

1) The light weight, small size and compactness of a semiconductor laser facilitate alignment of the optical axis.

The apparatus can be made compact, inexpensive and light in weight.

Since the position (of attachment) of the optical axis can be relatively freely selected because of the small size and light weight, there is greater freedom in designing the optical system. For example, the laser beam projection section and the light receiving section can be integrated with the remaining sections as in the embodiment described above.

2) A semiconductor laser requires injection of a driving current and various types of control can be realized using this current.

For production of a laser beam the laser must be supplied with the minimum required amount of injection current and for ensuring stable lasing, an amount of injection current larger than the required minimum is normally supplied. The fact that the amount of laser output varies in proportion to the amount of injection current can be used to correct for fluctuations in the power of the laser beam directed into the eye under examination, which fluctuations may occur because of various causes such as temperature change and time-course changes in the apparatus components, by detecting these changes and varying the injection current to restore the power to its original level. This is a major advantage of the semiconductor laser over the conventional gas laser.

3) Since the semiconductor laser produces a linearly polarized beam, the power of the laser beam can be regulated by including a polarizing plate in the laser beam projection optical system and rotating this plate as required. Alternatively, since the semiconductor laser is small, light-weight and compact, it itself can be rotated with the same effect.

4) There is a major and heretofore unavailable merit in the fact that, as will be understood from 2) and 3) above, it is possible to select from among more than one power regulating means in accordance with the conditions and the purpose at hand, or as required, to use these means in combination.

Where it is necessary to use a weak detection beam as in laser-based ophthalmological apparatuses, the ability to correct for power fluctuation in a manner such as described above is highly important. While up to now it has been common, for example, to extract a part of the detection beam for monitoring and to carry out power correction by processing data obtained from the extracted light through the use of a program, this method has the disadvantage of requiring a monitoring optical system. In contrast, the quantity of light output by a semiconductor laser can be directly regulated simply by regulating the current injected for driving the laser, which enables very simple and reliable regulation.

Further, the need to measure very weak scattered light has made conventional apparatuses highly sensitive to power fluctuation of the laser beam projection section. This has made it necessary to extract a portion of the laser beam for monitoring purposes and to correct the results of the measurement on the basis of the quantity of the extracted light using an appropriate program. However, direct modulation becomes possible when, as in the above embodiment, a semiconductor laser is used as the light source, and therefore the output on the projection light side can be regulated solely by the use of an electric circuit. Thus, too the apparatus can be simplified and reduced in cost.

Further, in the conventional apparatus for measuring protein concentration in the anterior chamber of the eye, the laser beam projection section and the slit beam projection section are integrated in one unit and the light receiving section and the observation section are integrated in another, and since light scattered at 90 degrees to the side is employed, observation from the observation section is limited to the 90-degree direction. This makes it impossible to use the apparatus as a slit lamp microscope. In the present invention, however, since the light receiving section 2 and the observation section 4 are fixed together, the slit beam projection section 3 can be rotated independently of the laser beam projection section 1 and the observation section 4 to which the light receiving section 2 is attached. Therefore, the apparatus is fully utilizable as a slit lamp microscope.

Furthermore, since the conventional practice has been to use a beam splitter for bringing the optical axes of the slit beam and the laser beam into registration, there has been a problem of a reduction in the light quantity in the slit and laser beams. In the present invention, however, the loss of slit beam light is reduced by separating the slit beam projection section and the laser beam illumination section. In addition, by separating the light receiving section 2 and the observation section 4, a brighter image can be viewed through the observation section, while making it easier to judge the alignment and observe the eye under examination. Moreover, the observation is also facilitated by the fact that the observation section 4 can be set directly in front of the eye under examination. Also, since the interference filter with a peak wavelength corresponding to the wavelength of the laser beam has been inserted into the light receiving section, the measurement need not be carried out in a dark room as has been required in the past but can be conducted in a semi-dark room.

In the embodiment described above, the optical axis of the laser beam and the optical axis at the eye under examination of the optical system 2' included in the light receiving section meet at an angle of about 90 degrees within a horizontal plane including the eye under examination E. Setting the angle at this value enables the judgment regarding alignment illustrated in FIGS. 5 to 9 to be made with maximum sensitivity. However, in a case where some reduction in this sensitivity is tolerable, the angle of intersection between the optical axis of the laser beam and that of the optical system 2' can be set at a value other than 90 degrees. For example, instead of using a common optical system between the light receiving section and the optical system 2' as in the aforesaid embodiment, it is possible to use separate systems.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. In an ophthalmological measurement apparatus in which a laser beam is directed into the eye under examination and a measurement value is output on the basis of the state of scattering of the laser beam within the eye under examination, the improvement comprising:
   a laser beam projection section for focusing a laser beam produced by a laser beam source at a predetermined point within an eye under examination;
   a light receiving section equipped with a photoelectric conversion element for receiving scattered laser light from the eye under examination;
   an alignment index projection section for forming at a predetermined point within the eye under examination an alignment index image for use in judging alignment between the apparatus and the eye under examination;
   an observation section for observing the state of the laser beam and of the light of the alignment index image at the eye under examination, the observation section including indices for indicating the positions within a field of vision of the observation section which are assumed by the light scattering points produced at the cornea of the eye under examination by the laser beam and the light of the alignment index image when the relative positions of the apparatus and the eye under examination are in predetermined alignment; and
   means for controlling the relative position between the eye under examination and the apparatus to cause light scattering points produced at the eye under examination by the laser beam and the light of the alignment index image to assume predetermined positions within the field of the observation section.

2. An apparatus according to claim 1, wherein the laser beam and the light of the alignment index image are of different colors.

3. An apparatus according to claim 1, wherein the alignment index projection section and the light receiving section have at least a part of their optical paths in common.

4. An apparatus according to claim 1, further comprising a slit beam projection section provided with a light source for projecting a slit beam image onto the eye under examination, the slit beam projection section having means for positioning itself with respect to the eye under examination independently of the laser beam projection section, the light receiving section, the alignment index projection section and the observation section.

5. An apparatus according to claim 1, wherein the laser beam source is a semiconductor laser.

6. An apparatus for making ophthalmological measurements comprising:
   projecting means movable toward and away from a patient's eye for projecting a beam of laser light at a spot in the eye;
   alignment projecting means movable toward and away from the eye for projecting an alignment light beam along an optical axis at the spot in the eye;
   receiving means for receiving laser and alignment light scattered from the spot in the eye along a part of the same optical axis;
   observing means for enabling an observer to observe the laser and alignment light scattered from the spot in the eye, the observing means including indicating means for indicating alignment positions of the laser and alignment light scattered from the spot in the eye; and
   means for moving the projecting means and alignment projecting means to positions relative to the eye so that the laser and alignment light scattered from the eye are observable at the alignment positions.

7. An apparatus according to claim 6; further comprising movable slit beam projecting means for projecting a slit beam image onto the spot in the eye.

8. An apparatus according to claim 7; wherein the slit beam projecting means includes means for moving the slit beam projecting means independently of the projecting means.

9. An apparatus according to claim 6; further comprising optical coupling means for optically coupling the alignment light beam with the scattered laser light received by the receiving means such that the alignment light beam and the scattered laser light have at least a part of their optical paths in common.

10. An apparatus according to claim 9; wherein the optical coupling means includes at least one beam splitter for projecting the alignment light beam onto the spot in the eye and for directing the scattered laser light onto the receiving means.

11. An apparatus according to claim 6; wherein the projecting means projects a beam of laser light having a first wavelength and the alignment projecting means projects an alignment light beam having a second wavelength.

12. An apparatus according to claim 6; wherein the receiving means includes at least one interference filter for filtering the scattered alignment light before it is received by the receiving means.

13. An apparatus according to claim 6; wherein the indicating means includes alignment indices for indicating the alignment positions.

* * * * *